United States Patent [19]
McLaurin, Jr.

[11] Patent Number: 5,370,117
[45] Date of Patent: Dec. 6, 1994

[54] IMMOBILIZATION SYSTEM FOR REPEATED USE IN IMAGING AND TREATING OF BRAIN TUMORS

[76] Inventor: Robert L. McLaurin, Jr., 1528 Iredell Dr., Raleigh, N.C. 27608

[21] Appl. No.: 176,224

[22] Filed: Jan. 3, 1994

[51] Int. Cl.$^5$ ............................ A61B 5/00; A61B 6/04
[52] U.S. Cl. .................... 128/653.1; 128/653.2; 128/653.5; 128/845; 128/857; 378/20; 378/68; 378/208; 606/130; 5/622
[58] Field of Search ............... 128/653.1, 653.2, 653.5, 128/846, 845, 857; 606/130; 378/20, 68, 208; 5/622

[56] References Cited

U.S. PATENT DOCUMENTS

| | | | |
|---|---|---|---|
| 3,982,132 | 9/1976 | Kay et al. | 378/208 |
| 4,463,758 | 8/1984 | Patil et al. | 606/130 |
| 4,550,713 | 11/1985 | Hyman | 606/130 |
| 4,638,798 | 1/1987 | Sheldon et al. | 128/653.1 |
| 4,884,566 | 12/1989 | Mountz et al. | 606/130 |
| 5,242,455 | 9/1993 | Skeens et al. | 128/653.1 |
| 5,281,232 | 1/1994 | Hamilton et al. | 128/653.5 |

OTHER PUBLICATIONS

Sales brochure for "Orfit Immobilization System" made by Nuclear Associates, division of Victoreen, Inc., undated.

Primary Examiner—K. M. Pfaffle
Attorney, Agent, or Firm—John G. Mills And Associates

[57] ABSTRACT

There is disclosed a patient immobilization system for repeated use in imaging and radiation therapy of a patient, the system comprising an immobilization plate, side rails mounted on the plate with mask studs outwardly projecting therefrom engaging a thermoplastic immobilization mask with at least two anchor bars holding the mask on said studs, wherein the improvement comprises a relatively rigid plastic arch having two ventricle leg portions and an apex, the lower ends of each of the leg portions being mounted on a respective one of the anchor bars; a flap of material outwardly projecting from the mask to a point adjacent the arch; a fixation member for mounting the outwardly projecting flap of material to the arch whereby the mask can be tightly held between the bars and the side rails on the studs and at a third point to the arch. Contrast material is provided at the apex of the arch and in each of the leg portions such that the x, y, and z axes can be shown in three-dimensional images of the patient.

8 Claims, 3 Drawing Sheets

IMMOBILIZATION SYSTEM FOR REPEATED USE IN IMAGING AND TREATING OF BRAIN TUMORS

FIELD OF INVENTION

This invention relates to immobilization devices and more particularly to immobilization system for repeated use in imaging and treating of brain tumors.

BACKGROUND OF INVENTION

Radiation therapy is the treatment of malignant tissue through the use of radiation. The guiding principle is that malignant tissue has diminished ability to repair the radiation damage; whereas normal, healthy tissue retains the ability to recover from radiation exposure. Therefore, if a tumor is exposed repeatedly to radiation, it should shrink in size or disappear and, as long as the neighboring healthy tissue is given adequate time to recover between treatments, there should not be excessive permanent damage.

The goal of radiation therapy is to deliver the radiation to the tumor itself while minimizing exposure of surrounding normal, healthy tissue. One important step in this process is treatment planning. Fractionated treatment, i.e. treatment involving the division of total radiation dose into twenty or thirty subparts, has been used for decades in an effort to maximize recovery time for healthy tissue, as well as to minimize side effects and complications from overexposure to radiation. Stereotactic techniques have been developed which employ accurate positioning of the patient during radiographic studies so as to improve the precision in locating tumors and the delivery of radiation. Over the years, the use of radiographic devices such as x-rays and CT scanners in this process has become common, and now the use of Magnetic Resonance Imagery technology (MRI) is being actively investigated. These imaging techniques enable the radiation oncologist to look inside the body and avoid invasive surgery which might otherwise be necessary to locate and describe the lesions.

The development of treatment planning systems has been rapidly evolving. The x-ray pictures produced by traditional simulators provide the physician with a "beam's-eye view" of a tumor within a patient. This technology had the disadvantage that it helps to visualize only hard structures within the body, such as bones, but would not provide accurate and clear pictures of soft tissues, i.e. tumors or sensitive organs.

Following the development of the Computerized Tomography or CAT-scan technology, a computer simulator program was developed which is able to produce three-dimensional images showing soft tissue and tumor structures. This technology represented a great advance over the prior art, but it has been slowly adopted because of three major drawbacks. First, to develop the three-dimensional images to depict the tumor and other sensitive organs, a technician must abstract information from CT scans slice by slice, which is very time-consuming. Second, because of the abstraction process, one loses much of the anatomy that is desirable in preparing a treatment plan. Finally, this technology has the disadvantage that the dosing curves that are superimposed online drawings of the anatomy are very difficult for the physician to interpret.

In radiation oncology, it has long been important to immobilize the patient during treatment and radiographic examination in order to assure that radiation is delivered exactly where it is needed and that tumors and surrounding normal structures are precisely located. Existing immobilization systems, however, have proven incompatible with MRI-based techniques. Because of the size limitations of the MRI magnetic head coil, it is virtually impossible to utilize a standard immobilization system. In addition, the presence of the stainless steel structures present in classic stereotactic immobilization systems cause severe distortion of the MRI image.

A three-dimensional treatment planning software product has been developed by George Sheroure, Phd. under the name of Gratis. This software includes a program called Virtual Simulator which takes information abstracted from CT scans and develops three-dimensional images. This is strictly for CT scans and there is no suggestion of applying the program to or MRI technology.

BRIEF DESCRIPTION OF INVENTION

After much research and study into the above mentioned problems, the present invention has been developed to allow precision delivery of radiation to brain tumors.

The above is accomplished through proprietary enhancements to the Virtual Simulator Software so that radiation dose distribution can be portrayed directly on MRI images. The MRI-oriented Virtual Simulator displays the tumor and sensitive organs from "beam's-eye view" without the necessity of abstraction from other scans and provides better contrast and improved image definition for matching of isodose curves.

The results of the above enhancements, coupled with the immobilization system of the present invention, allows fractionated radiation treatment on a precision basis since the patient can be readily and repeatedly placed in the same position. The present immobilization template is non-invasive, i.e. no screws or pneumatic fasteners are applied to the skull, it is capable of being applied in a short amount of time and after minimal training, and it improves upon the use of commonly available thermal plastic masks by adding another point of anchor to a rigid Plexiglass arch that is compact enough to fit within the magnetic resonance image magnetic coil.

When the mask system of the present invention is used in combination with the commonly available laser-beam alignment systems in most treatment centers, precise location of the patient and the tumor can be realized in repeated visits for treatment.

Analysis and treatment has shown that, despite the slight inherent distortions of magnetic resonant or MRI technology, tumors located within the skull can be repeatedly irradiated with an accuracy that exceeds prior treatment methods. The MRI distortion noted above introduces no more than one to two millimeters of variation which is far better than accuracy necessary for the delivery of precision radiation.

In summary, the combination of the immobilization system and the imaging system allows the use of small field sizes, i.e. areas where doses are delivered, and offers significant reduction in the volume of normal tissues exposed to radiation while providing enhanced flexibility in the precise dose delivery. A reduction in the field size has been demonstrated to produce a reduction in accute side effects which will result in fewer long term complications.

The following reference represents the closest prior art of which the inventor is aware:

CONCISE EXPLANATION OF REFERENCES

The Orfit Immobilization System produced by Nuclear Associates, division of Victoreen, Inc., 1100 Voice Road, Carle Place, New York 11514-0349 is a repeated positioning immobilization system for radiation therapy. This system includes a mask that can be conformed to the patient's face and secured on each side of the head. Lateral movement of the head, however, can still occur and there are, of course, no built in reference points.

In view of the above it is an object of the present invention to provide an immobilization system for repeated use in imaging and treating of brain tumors.

Another object of the present invention is to provide an immobilization system including a thermal plastic mask with a rigid plastic arch designed specifically to fit within the confines of an MRI head coil.

Another object of the present invention is to provide a patient immobilization system that is non-invasive, eliminates the presence of stainless steel and yet is extremely stable for repeated use in imaging and treating of brain tumors and lesions.

Another object of the present invention is to provide an immobilization system with marker means to a interact with laser beam alignment systems to precisely position the patient and tumor for imaging and treating.

Another object of the present invention is to provide oil filled markers in the rigid plastic arch which serve as markers on the enhanced MRI images.

Another object of the present invention is to provide permanent laser-beam markers on an immobilization system so precise relocation of the patient and tumor can be realized.

Other objects and advantages of the present invention will become apparent and obvious from a study of the following description and the accompanying drawings which are merely illustrative of such invention.

DETAILED DESCRIPTION OF INVENTION

Figure 1:
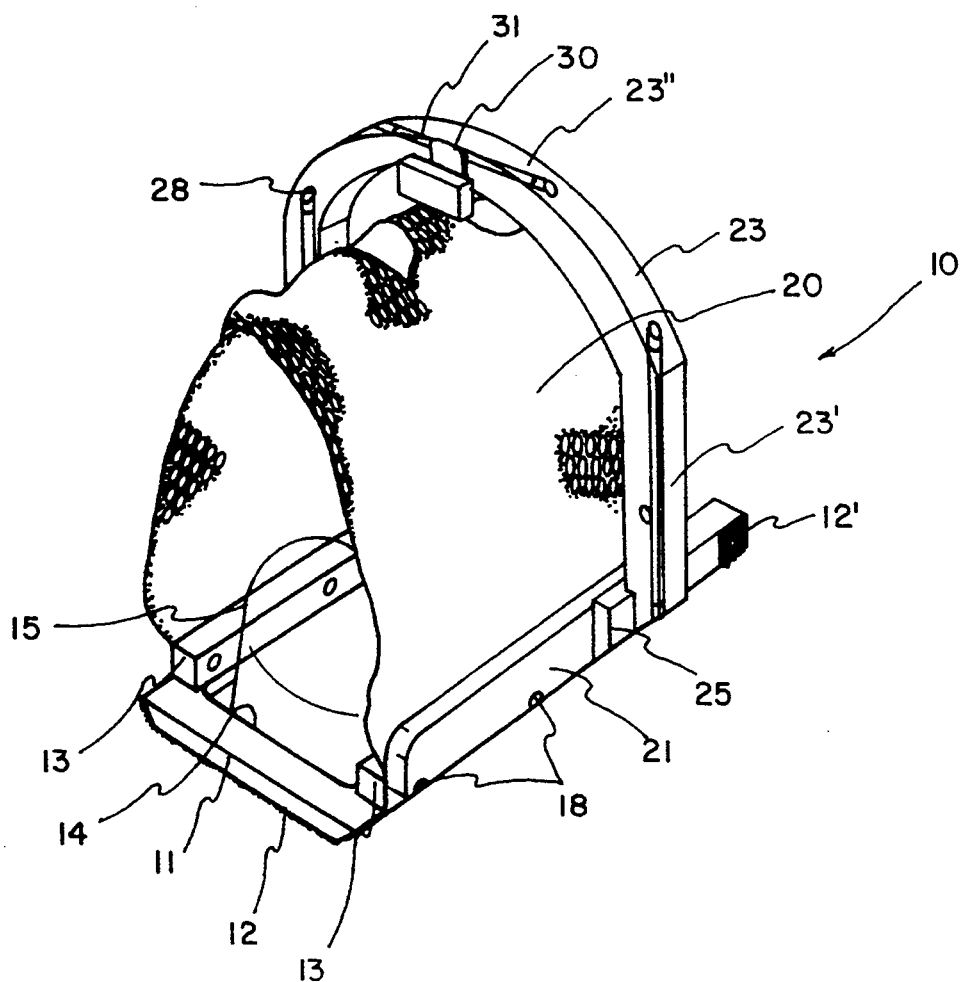
FIG. 1 is a perspective view of the immobilization system of the present invention.
Figure 2:
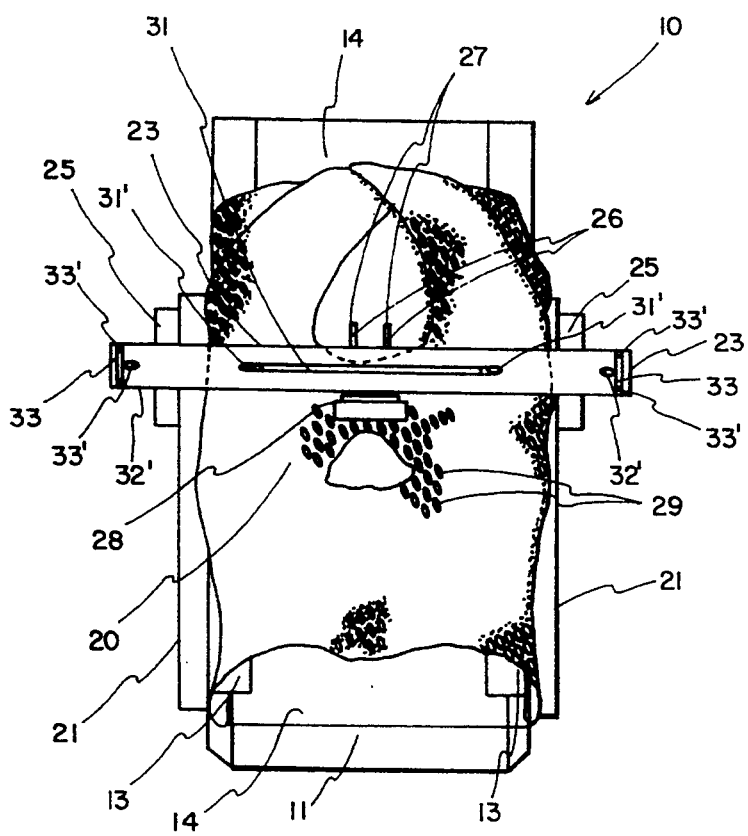
FIG. 2 is a top plan view thereof.

With further reference to the drawings, the immobilization system of the present invention, indicated generally at 10, includes an immobilization plate 11. A pair of side rails 13 are mounted on opposite edges of said immobilization plate 11 by fusion or other suitable methods. If desired, the plate 11 and the pair of rails 13 can be formed from a single piece of clear plastic material such as Plexiglass.

Extending from the outside of the side rails 13 and across the bottom of the immobilization plate 11 of the proximal and distal ends of the immobilization system 10 of the present invention is a strip of hook material 12 and 12' of the type sold under the brand name Velcro. A loop material can be provided on the imaging and x-ray tables or platforms (not shown) for securing the system 10 thereto during use.

A slight depression 14 is provided in the base 11 between the pair of side rails 13. This depression is box shaped and is adapted to receive neck and head rest 15. Since this neck and head rest is approximately the same width as the depression 14 but not as long, it can slide longitudinally back and forth for proper adjustment in holding the head 16 of the patient 17 within the immobilization system 10 of the present invention.

Figure 5:
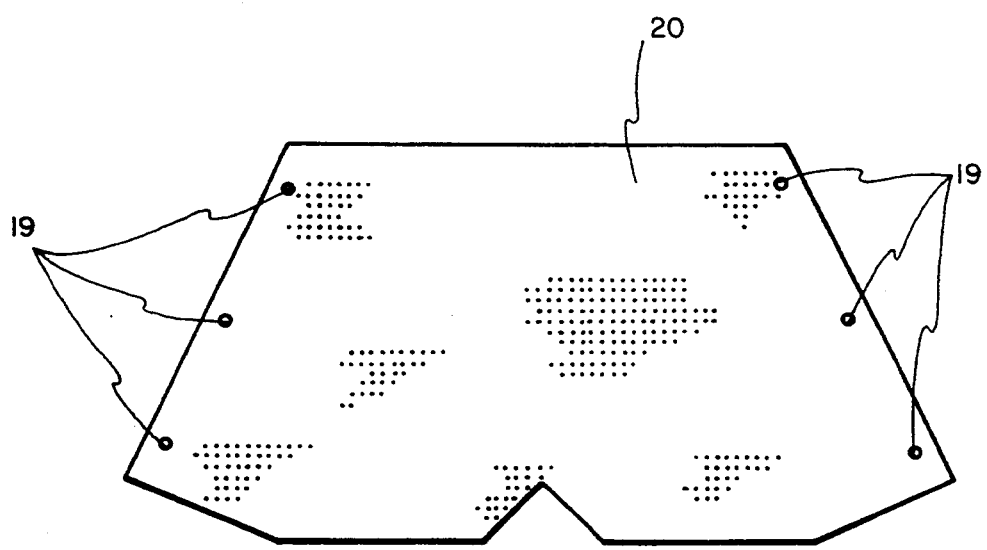
FIG. 5 is a plan view of a pre-cut thermoplastic mask form.

A plurality of mask mounted studs 18 are provided on the outer walls of the pair of side rails 13 on plate 11. These mask studs are spaced a standard distance apart so that they can be used with readily available thermoplastic mask material which comes in sheet form with the holes spaced therein as can be seem clearly in FIG. 5.

The pre-cut thermoplastic material is formed over the head of the patient and openings 19 in the mask 20 are slipped over the mask studs 18.

A pair of Plexiglas anchor bars 21 have openings therein that match with the mask studs 18 and are adapted to engage said studs to hold the mask 20 in place.

In the prior art, one or more vertical pins were used to hold the anchor bars 21 in place on the mask studs with the edges of the mask therebetween as clearly shown in the Nuclear Associates reference.

A problem with the prior art thermoplastic mask is that it will wobble from side to side and thus is not a complete immobilization device and cannot be counted on to hold the head of the patient in the same position for repeated use in imaging and treating of the patient's brain tumor.

To overcome the above problem of flexing the present invention has been developed with includes a relatively rigid Plexiglas arch 23 with the lower ends of its vertical legs 23' being mounted in a vertical slot 24 in arch base 25. This arch base is fixedly secured by fusion or other suitable methods to the outer edge of the anchor bars 21 as can clearly be seen in the Figures.

Figure 4:
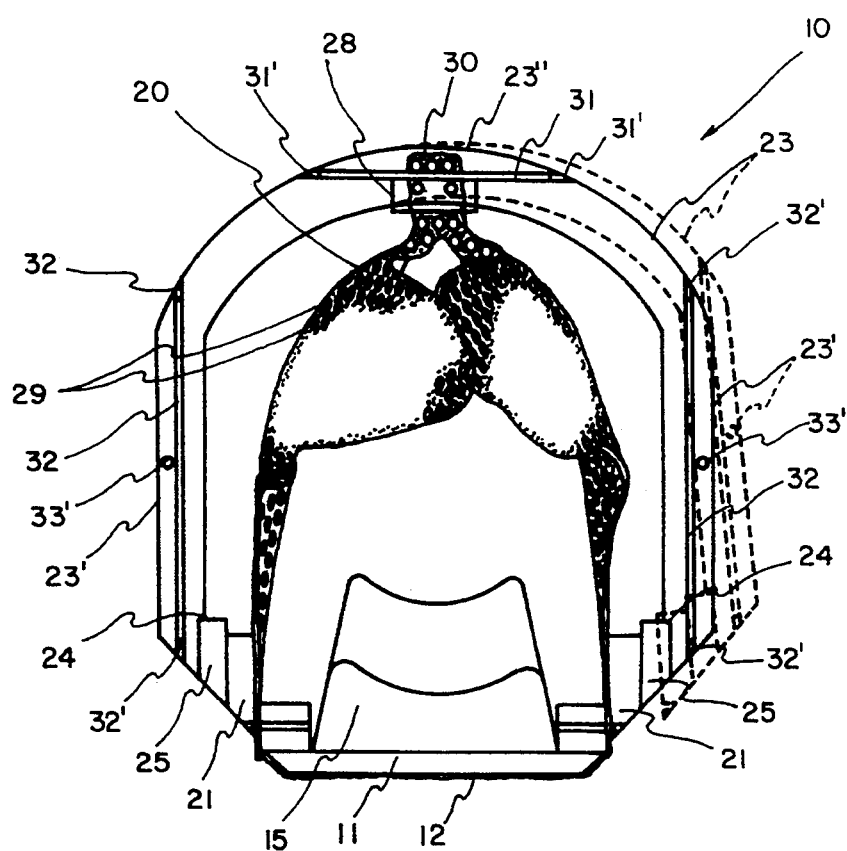
FIG. 4 is an end elevational view thereof.

In the apex 23" of Plexiglas arch 23 are two horizontal openings 26 adapted to receive the two pins 27 outwardly extending from fixation clip 28. The spacings of the pins 27 are equal to the spacing of three of the mesh openings 29 in the thermoplastic mask 20. A flap of mask material 30 is upwardly disposed when the thermal plastic mask is being fitted to the patient. This flap is at least three openings wide so that during the setting process of the mask material, the pins 27 of the fixation clip 28 can be passed through the upper end of the flap 30 of the mask material, as can clearly be seen in FIG. 4.

A contrast column 31 is drilled horizontally across the apex 23" of Plexiglas arch 23. This column is filled with any suitable type of oil, such as baby oil, and is sealed at its ends 31'. In a side MRI image, the oil-filled column 31 will show up as a white dot. This column is the X-axis of the three-dimensional imaging.

A vertical contrast column 32 is drilled in each of the vertical legs 23' of Plexiglas arch 23. Each of these columns are filled with oil and are sealed at their ends 32'. Contrast columns 32 are used as Y-axis in the MRI three dimensional imaging.

Finally, horizontal contrast columns 33 are drilled through the central portion of the vertical legs 23' outside of the vertical contrast columns 32 therein. Again the horizontal contrast columns 33 are filled with oil and are sealed at their ends 33'. These columns act as the Z-axis in three-dimensional imaging.

Figure 3:
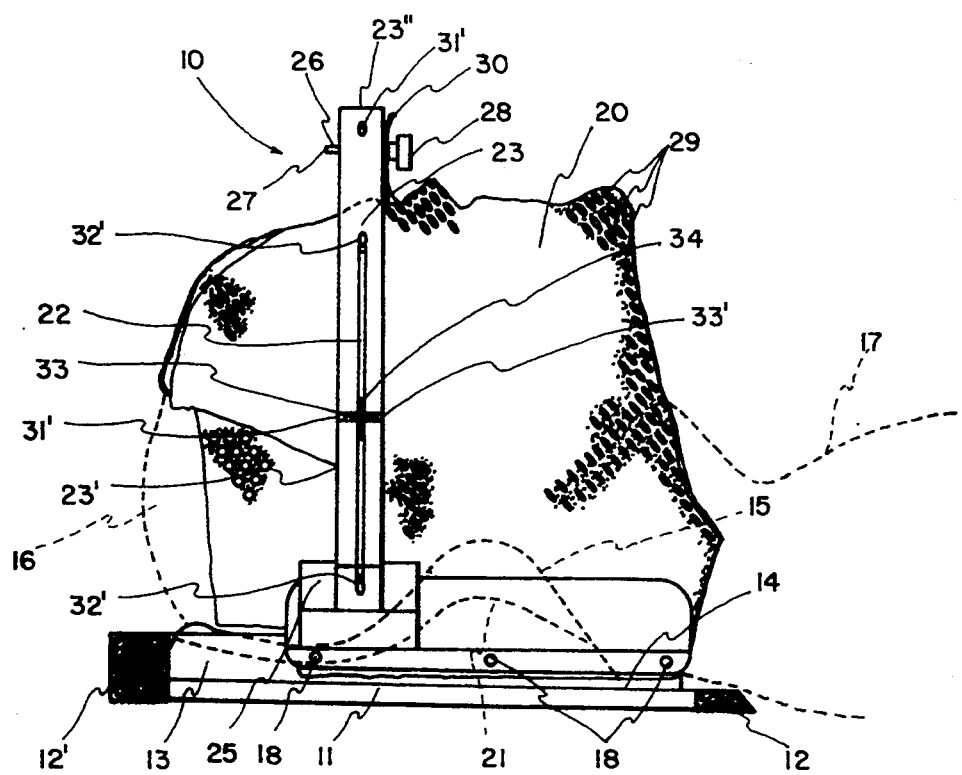
FIG. 3 is a side elevational view thereof.

A +-shaped laser beam marker 34 is provided on the exterior of each of the arch legs 23 at the juncture of the vertical contrast column 32 and the horizontal contrast column 33 when viewed in side elevational view as seen in FIG. 3.

The two Plexiglas anchor bars 21 and their associated Plexiglas arch bases 25 and associated Plexiglas arch 23 form an integral unit. When at rest with no tension applied thereto, the interior of the anchor bars 21 are the same distance apart as the exterior of the side rails 13. Although the Plexiglas arch 23 is relatively rigid, it can be deformed slightly by pulling the anchor bars apart a short distance as shown in dotted lines in FIG. 4.

When the openings 19 in one side of the mask 20 have been placed over the mask studs 18 with the associated anchor bar mounted on such studs exterior of the mask, then the openings 19 on the opposite side of the mask can be mounted on the mask studs 18 of the opposite side rail 13. The other anchor bar 21 of the arch 23 is then pulled outwardly to clear the outer ends of the mask studs 18 so that such anchor bar can be moved into engagement with such studs. Once this has been accomplished, pressure is released from the anchor bar and the arch resumes its original shape with the interior of the anchor bars holding the mask 20 tightly against the exterior of the side rails 13. No further pins, bolts or other means are required to hold the thus assembled immobilization system 10 in place.

From the above it can be seen that the present invention has the advantage of providing a simple, relatively inexpensive and yet highly efficient immobilization system for MRI imaging and radiation treatment of brain tumors. Each time a patient returns for further imaging and treatment, such patient can repeatedly be placed in the same position by laser-beam locators. Additionally, the system is simple to place on and remove from the patient.

The term "sides," "ends," "vertical," "horizontal," etc. have been used herein merely for convenience to describe the present invention and its parts as oriented in the drawings. It is to be understood, however, that these terms are in no way limiting to the invention since such invention may obviously be disposed in different orientations when in use.

The present invention may, of course, be carried out in other specific ways than those herein set forth without departing from the spirit and essential characteristics of such invention. The present embodiments are, therefore, to be considered in all respects as illustrative and not restrictive, and all changes coming within the meaning and equivalency range of the appended claims are intended to be embraced therein.

What is claimed is:

1. A patient immobilization system for repeated use in imaging and radiation therapy of a patient, said system including an immobilization plate, side rails mounted on said plate with mask studs outwardly projecting therefrom engaging a thermoplastic immobilization mask with at least two anchor bars holding said mask on said studs, the improvement comprising: a relatively rigid plastic arch having two verticle leg portions and an apex, the lower ends of each of said legs being mounted on a respective one of said anchor bars; means outwardly projecting from said mask to a point adjacent said arch; and fixation means for mounting said outwardly projecting means to said arch whereby the mask can be tightly held between said bars and said side rails on said studs and at a third point to said arch.

2. The immobilization system of claim 1 wherein the outwardly projecting means from said mask is a flap of mask material.

3. The immobilization system of claim 1 wherein a horizontal contrast means for providing a contrast of an x-axis in three-dimensional images is provided at the apex of the arch; a vertical contrast means for providing a contrast of a y-axis in three-dimensional images is provided at each of the legs of said arch; and a horizontal contrast means for providing a contrast of a z-axis in three-dimensional images is provided at each of said legs whereby the x, y and z axes can be shown in three dimensional images of said patient.

4. The immobilization system of claim 3 wherein the contrast means are oil.

5. The immobilization system of claim 3 wherein the contrast means are oil-filled columns.

6. The immobilization system of claim 5 wherein the oil-filled contrast columns are drilled in the apex and legs of the arch with the oil sealed therein.

7. The immobilization system of claim 1 wherein the fixation means is a plastic clip.

8. The immobilization system of claim 7 wherein the fixation clip includes at least one pin-like member for engaging the outwardly projecting means and at least one opening in said arch.

* * * * *